United States Patent [19]

Sottery et al.

[11] Patent Number: 5,229,104
[45] Date of Patent: Jul. 20, 1993

[54] ARTIFICIAL TANNING COMPOSITIONS CONTAINING POSITIVELY CHARGED PAUCILAMELLAR VESICLES

[75] Inventors: John P. Sottery, Milford; George E. Deckner, Trumbull, both of Conn.

[73] Assignee: Richardson-Vicks Inc., Cincinnati, Ohio

[21] Appl. No.: 693,263

[22] Filed: Apr. 29, 1991

[51] Int. Cl.$^5$ ............ A61K 7/42; A61K 7/44; A61K 7/48; A61K 9/10
[52] U.S. Cl. ............ 424/59; 424/60; 424/63; 424/195.1; 424/450; 514/167; 514/251; 514/458; 514/474; 514/725; 514/847; 514/938
[58] Field of Search ............ 424/450, 59, 60, 63

[56] References Cited

U.S. PATENT DOCUMENTS

| | | | |
|---|---|---|---|
| 3,184,388 | 5/1965 | Kalopissis | 167/90 |
| 3,272,713 | 9/1966 | Runge | 167/90 |
| 3,920,808 | 11/1975 | Fusaro | 424/59 |
| 4,145,413 | 3/1979 | Usdin et al. | 424/63 |
| 4,217,344 | 8/1980 | Vanlerberghe et al. | 424/450 |
| 4,247,411 | 1/1981 | Vanlerberghe et al. | 424/450 |
| 4,419,343 | 12/1983 | Pauly | 424/59 |
| 4,772,471 | 9/1988 | Vanlerberghe et al. | 424/450 |
| 4,792,331 | 12/1988 | Philippot et al. | 604/187 |
| 4,830,857 | 5/1989 | Handjani et al. | 424/450 |
| 4,832,943 | 5/1989 | Grollier et al. | 424/59 |
| 4,853,228 | 8/1989 | Wallach et al. | 424/450 |
| 4,897,308 | 1/1990 | Vanlerberghe et al. | 424/450 |
| 4,917,951 | 4/1990 | Wallach | 424/450 |
| 4,942,038 | 7/1990 | Wallach | 424/450 |
| 5,154,854 | 10/1992 | Zabotto et al. | 252/312 |

FOREIGN PATENT DOCUMENTS

| | | |
|---|---|---|
| 77-03895Y/03 | 12/1976 | Belgium . |
| 90-320544/43 | 8/1990 | Canada . |
| 2009607 | 8/1990 | Canada . |
| 89-159409/22 | 5/1989 | European Pat. Off. . |
| 318369 | 5/1989 | European Pat. Off. . |
| 90-248499/33 | 8/1990 | European Pat. Off. . |
| 382619 | 8/1990 | European Pat. Off. . |
| 91-024247/04 | 1/1991 | European Pat. Off. . |
| 409690 | 1/1991 | European Pat. Off. . |
| 91-119499/17 | 4/1991 | European Pat. Off. . |
| 89-294897/41 | 8/1989 | France . |
| 90-099893/14 | 10/1989 | German Democratic Rep. . |
| 90/06747 | 6/1990 | PCT Int'l Appl. . |
| 90/07924 | 7/1990 | PCT Int'l Appl. . |
| 83-825600/47 | 2/1983 | U.S.S.R. . |
| 2078543 | 7/1980 | United Kingdom . |
| 2189457 | 10/1987 | United Kingdom . |

OTHER PUBLICATIONS

Handjani-Vila, R. M. et al. "Dispersions of Lamellar Phases of Non-Ionic Lipids in Cosmetic Products", International Journal of Cosmetic Science, vol. 1, pp. 303-314 (1979) (Reference 30).
CA98(16):132150g, Oct. 1, 1982, Spain.
CA72(20):103635b, Mar. 15, 1969, Czechoslovakia.
Carton Copy, "Effet Du Soleil: Self-Tanning Moisture Care with Non-Ionic Microspheres For the Face", Lancome, New York, NY (believed to have been first marketed in the United States in 1990) (Reference 31).

*Primary Examiner*—Dale R. Ore
*Attorney, Agent, or Firm*—Anthony D. Sabatelli; David K. Dabbiere; Douglas C. Mohl

[57] ABSTRACT

The present invention relates to oil-in-water emulsion compositions useful for imparting an artificial tan to human skin. These emulsions contain paucilamellar lipid vesicles, i.e. vesicles comprising several concentric lipid bilayers, encapsulating an aqueous dihydroxyacetone solution. The vesicles comprise a polyoxyalkylene alkyl ether, a sterol, a quaternary ammonium compound, and optionally, a non-surface active oil. In further embodiments, these emulsion compositions contain one or more sunscreens, and are also useful for protecting human skin from the harmful effects of sunlight and other sources of ultraviolet radiation. The present invention also relates to methods for preparing these compositions, methods for providing an artificial tan to human skin, and methods for protecting human skin from the harmful effects of ultraviolet radiation.

28 Claims, No Drawings

ARTIFICIAL TANNING COMPOSITIONS CONTAINING POSITIVELY CHARGED PAUCILAMELLAR VESICLES

TECHNICAL FIELD

The present invention relates to oil-in-water emulsion compositions useful for imparting an artificial tan to human skin. These emulsions contain paucilamellar lipid vesicles, i.e. vesicles comprising several concentric lipid bilayers, encapsulating an aqueous dihydroxyacetone solution. The vesicles comprise a polyoxyalkylene alkyl ether, a sterol, a quaternary ammonium compound, and optionally, a non-surface active oil. In further embodiments, these emulsion compositions contain one or more sunscreens, and are also useful for protecting human skin from the harmful effects of sunlight and other sources of ultraviolet radiation. The present invention also relates to methods for preparing these compositions, methods for providing an artificial tan to human skin, and methods for protecting human skin from the harmful effects of ultraviolet radiation.

BACKGROUND OF THE INVENTION

It is generally known that dihydroxyacetone, when applied topically to human skin, will produce a tanned appearance, i.e. an artificial tan. U.S. Pat. No. 4,708,865, to Turner, issued Nov. 24, 1987 describes the use of hydro-alcoholic solutions of dihydroxyacetone for tanning the skin; U.S. Pat. No. 4,466,805, to Welters, issued Aug. 21, 1984 describes hair and skin coloring formulations containing dihydroxyacetone; and U.S. Pat. No. 2,949,403, to Andreadis et al., issued Aug. 16, 1960 describes artificial tanning formulations containing dihydroxyacetone in an oleaginous base. However, it is also known that emulsion products containing dihydroxyacetone have a short shelf life, tending to darken and develop disagreeable off-odors over time with a concomitant loss of emulsion integrity. Dihydroxyacetone is relatively sensitive to heat, light, moisture, and alkaline pH. Dihydroxyacetone can react with other ingredients in a formulation, especially with nitrogen-containing compounds, such as amines, amino acids, and the like. In fact, without being limited by theory, dihydroxyacetone is believed to provide an artificial tan to human skin by its reaction with the nitrogen containing proteins of the skin. See L. Goldman et al., "Investigative Studies with the Skin Coloring Agents Dihydroxyacetone and Glyoxal", *The Journal of Investigative Dermatology*, vol. 35, pp 161-164 (1960); and E. Wittgenstein et al., "Reaction of dihydroxyacetone (DHA) with Human Skin Callus and Amino Compounds", *The Journal of Investigative Dermatology*, vol. 36, pp. 283-286 (1961).

The manufacture of liposomes, i.e. lipid vesicles, and their use for the delivery of a wide variety of materials is well-known. See Gregoriadis, G., ed. *Liposome Technology* vols. 1-3, 1984 (CRC Press, Boca Raton, Fla.). Most of the commonly used liposomes are single-layered vesicles prepared from phospholipids. The reason for this is that phospholipids are the principal structural components of natural membranes. However, phospholipids are susceptible to enzymatic degradation, autoxidation, and acidic pH conditions, and are exceedingly expensive to prepare. Furthermore, phospholipid vesicles are relatively fragile, tending to rupture, coalesce, and release their encapsulates. To avoid these disadvantages, there has been a movement towards the development of multilayered (i.e. multilamellar) vesicles prepared from a variety of lipids and surfactants. However, multilayered vesicles are generally more difficult to produce than conventional liposomes, and their encapsulation volumes tend to be small. Paucilamellar lipid vesicles overcome the disadvantages of conventional multilayered liposomes by providing both a stable multilayered lipid structure and a relatively large central cavity. Paucilamellar lipid vesicles are described in U.S. Pat. No. 4,911,928, to Wallach, issued Mar. 27, 1990. Furthermore, paucilamellar vesicles are especially suited for encapsulating aqueous solutions of hydrophilic materials. In particular, paucilamellar vesicles made by replacing conventional phospholipids with acid-stable/compatible surfactants such as polyoxyalkylene alkyl ethers have the additional advantage of providing an acid-stable liposomal system useful for encapsulating acidic materials such as dihydroxyacetone in formulations having an acidic pH.

Currently available artificial tanning products have the disadvantage of not providing the desired control over color development of the tan. Artificial tans are often either too light or too dark, and tend to be too orange, uneven, or unnatural in appearance. Furthermore, artificial tans tend to take too long to develop, and once obtained, tend to fade too quickly and unevenly. Therefore, it would be highly desirable to provide dihydroxyacetone containing products which are chemically and physically stable, which are aesthetically pleasing, and which overcome these color development limitations. Products which overcome these disadvantages can be achieved through the use of paucilamellar liposome systems for delivering dihydroxyacetone from an oil-in-water emulsion composition.

Sunscreens are the most common agents used for sun protection. However, sunscreens also have the disadvantage of preventing or greatly diminishing the cosmetically desirable tanning response. Therefore, it would be highly desirable to provide protection from the harmful effects of ultraviolet radiation, and yet at the same time deliver a tanned appearance to the skin.

Furthermore, even if an individual is willing to accept the risks associated with exposure to ultraviolet radiation in order to obtain a tan, there are situations in which it may not be practical or even possible to do so because of time constrains, weather conditions, time of day, season of the year, geographic limitations, unavailability of an artificial ultraviolet radiation source, and the like. Therefore, it would be highly desirable to provide products that can deliver a tanned appearance whenever desired, without the need for ultraviolet radiation.

It is therefore an object of the present invention to provide oil-in-water emulsion compositions containing dihydroxyacetone in paucilamellar vesicles for imparting an artificial tan to human skin. Another object of the present invention is to provide emulsion compositions for imparting an artificial tan which exhibit a high degree of chemical and physical stability and which are aesthetically appealing to consumers. A further object of the present invention is to provide compositions for both imparting an artificial tan to human skin and also for protecting the skin from ultraviolet radiation. A still further object of the present invention is to provide a method for artificially tanning human skin. It is another object of the present invention to provide a method for both artificially tanning human skin and for providing protection against ultraviolet radiation.

These and other objects of this invention will become apparent in light of the following disclosure.

SUMMARY OF THE INVENTION

The present invention relates to an artificial tanning oil-in-water emulsion composition having a pH from about 2.5 to about 7, comprising:

(a) from about 1% to about 50% of an oil phase;
(b) from about 0.1% to about 10% of at least one emulsifier;
(c) from about 0.1% to about 5% of at least one thickener;
(d) from about 10% to about 95% of an aqueous phase;
(e) from about 0.1% to about 20% of dihydroxyacetone; and
(f) from about 0.1% to about 20% on a dry weights basis of paucilamellar liposomal vesicles having a diameter of from about 100 nm to about 500 nm, said vesicles being dispersed in the aqueous phase (d) and wherein said vesicles comprise a polyoxyalkylene alkyl ether, a sterol, and a quaternary ammonium compound and further wherein said vesicles encapsulate an internal aqueous phase.

All percentages and ratios used herein are by weight and all measurements are at 25° C., unless otherwise indicated.

DETAILED DESCRIPTION OF THE INVENTION

Emulsion Compositions

The compositions of the instant invention are in the form of oil-in-water emulsions whereby the oil phase can contain typical oil-soluble components and the water phase can contain typical water-soluble materials. These types of emulsions are preferred because of their desirable aesthetic properties and their utility as vehicles for the dihydroxyacetone, the paucilamellar liposomes, and the other essential and optional components of this invention. The emulsions of the instant invention comprise from about 1% to about 50% of an oil phase and from about 10% to about 95% of an aqueous phase. These emulsions can cover a broad range of consistencies including lotions, light creams, heavy creams, and the like.

To obtain an artificial tan using the emulsions of the instant invention, an effective amount of the emulsion is topically applied to human skin. By "effective" is meant an amount sufficient to provide an artificial tan when the composition is topically applied, but not so much as to cause any side effects or skin reactions. Quantities of emulsion which can be topically applied to provide an artificial tan are about, but not limited to, 2 mg/cm$^2$.

pH Requirements

The pH of a formulation is an important factor in determining the stability of the dihydroxyacetone. For example, it is well known that dihydroxyacetone rapidly degrades at extremes of alkaline pH. Suppliers of dihydroxyacetone suggest a preferred formulation pH range of between 4 and 6, and recommend the use of a buffer system to stabilize the pH value at about 5. See "Dihydroxyacetone for Cosmetics", E. Merck Technical Bulletin, 03-304 110, 319 897, 180 588, this reference being incorporated herein by reference in its entirety. However, the compositions of the instant invention preferably do not contain a buffer. The unbuffered compositions of the instant invention have a pH range from about 2.5 to about 7, preferably from about 3 to about 6, and most preferably from about 3 to about 4.5.

Dihydroxyacetone

An essential component of the present compositions is dihydroxyacetone. Dihydroxyacetone, which is also known as DHA or 1,3-dihydroxy-2-propanone, is a white to off-white, crystalline powder having a characteristic sweet, cooling taste. The compound can exist as a mixture of monomers and dimers, with the dimer predominating. Heating or melting dimeric dihydroxyacetone converts the material into the monomeric form. The conversion of the dimer to the monomer also takes place in aqueous solution. See *The Merck Index*, Tenth Edition, entry 3167, p. 463 (1983), this reference being incorporated herein by reference in its entirety.

The dihydroxyacetone of the emulsion compositions of the instant invention is present from about 0.1% to about 20%, preferably from about 2% to about 7%, and most preferably from about 3% to about 5%.

Thickener

Another essential component of the compositions of the instant invention is a thickener. Examples of such thickeners which can be employed include, but are not limited to, xanthan gum, magnesium aluminum silicate, guar gum, cationic guar gum, Rhamsan Gum (available from Kelco Chemical co.), kelp. algin and alginate salts, starch and starch derivatives, hydroxypropylcellulose, hydroxyethylcellulose, carboxymethylcellulose, methylcellulose, ethylcellulose, smectite clay thickeners such as hectorite and bentonite, sodium magnesium silicate and mixtures thereof. Examples of suitable thickeners are disclosed in Lochhead, R.Y., "Encyclopedia of Polymers and Thickeners", *Cosmetics & Toiletries*, vol. 103, no. 12, pp 99–129 (1988); Meer, G., "Natural Gum Polymers as Ingredients in Cosmetics", *Cosmetics & Toiletries*, vol. 99, no. 6, pp. 61–64 (1984); and Freeland, M. S. "Cationic Guar Gum", *Cosmetics & Toiletries*, vol. 99, no. 6, pp 83–87 (1984); these three references are incorporated herein by reference in their entirety. Preferred thickeners include magnesium aluminum silicate and xanthan gum and mixtures thereof. The compositions of the instant invention comprise from about 0.1% to about 5% thickener, preferably from about 0.25% to about 2%, and most preferably from about 0.5% to about 1%.

Emulsifier

Another essential component of the compositions of the instant invention is at least one emulsifier. Suitable emulsifiers can include any of a wide variety of nonionic, cationic, anionic, and zwitterionic emulsifiers disclosed in the prior patents and other references. See McCutcheon's, *Detergents and Emulsifiers*, North American Edition (1986), published by Allured Publishing Corporation; U.S. Pat. No. 5,011,681 to Ciotti et al, issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, and mixtures thereof.

The emulsifiers can be used individually or as a mixture of two or more and comprise from about 0.1% to about 10%, preferably from about 1% to about 7%, and most preferably from about 1% to about 5% of the compositions of the present invention.

Carboxylic Acid Copolymer

In addition to the above described emulsifiers, the emulsifier component can also comprise one or more carboxylic acid copolymers (i.e. an acrylic acid copolymer). These copolymers consist essentially of a colloidally water-soluble polymer of acrylic acid crosslinked with a polyalkenyl polyether of a polyhydric alcohol, and optionally an acrylate ester or a polyfunctional vinylidene monomer.

Preferred copolymers useful in the present invention are polymers of a monomeric mixture containing 95.9 to 98.8 weight percent of an olefinically unsaturated carboxylic monomer selected from the group consisting of acrylic, methacrylic and ethacrylic acids; about 1 to about 3.5 weight percent of an acrylate ester of the formula:

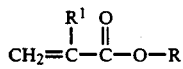

wherein R is an alkyl radical containing 10 to 30 carbon atoms and $R^1$ is hydrogen, methyl or ethyl; and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

Preferably, these polymers contain from about 96 to about 97.9 weight percent of acrylic acid and from about 2.5 to about 3.5 weight percent of acrylic esters wherein the alkyl group contains 12 to 22 carbon atoms, and $R^1$ is methyl, most preferably the acrylate ester is stearyl methacrylate. Preferably, the amount of cross-linking polyalkenyl polyether monomer is from about 0.2 to 0.4 weight percent. The preferred crosslinking polyalkenyl polyether monomers are allyl pentaerythritol, trimethylolpropane diallylether or allyl sucrose. These polymers are fully described in U.S. Pat. No. 4,509,949, to Huang et al., issued Apr. 5, 1985, this patent being incorporated herein by reference.

Other preferred copolymers useful in the present invention are the polymers which contain at least two monomeric ingredients, one being a monomeric olefinically-unsaturated carboxylic acid, and the other being a polyalkenyl, polyether of a polyhydric alcohol. Additional monomeric materials can be present in the monomeric mixture is desired, even in predominant proportion.

The first monomeric ingredient useful in the production of these carboxylic polymers are the olefinically-unsaturated carboxylic acids containing at least one activated carbon-to-carbon olefinic double bond, and at least one carboxyl group. The preferred carboxylic monomers are the acrylic acids having the general structure

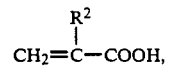

wherein $R^2$ is a substituent selected from the class consisting of hydrogen, halogen, and the cyanogen (—C≡N) groups, monovalent alkyl radicals, monovalent alkaryl radicals and monovalent cycloaliphatic radicals, Of this class, acrylic, methacrylic, and ethacrylic acid are most preferred. Another useful carboxylic monomer is maleic anhydride or the acid. The amount of acid used will be from about 95.5 to about 98.9 weight percent of the total monomers used. More preferably the range will be from about 96 to about 97.9 weight percent.

The second monomeric ingredient useful in the production of these carboxylic polymers are the polyalkenyl polyethers having more than one alkenyl ether grouping per molecule. The most useful possess alkenyl groups in which an olefinic double bond is present attached to a terminal methylene grouping, $CH_2=C<$.

The additional monomeric materials which can be present in the polymers include polyfunctional vinylidene monomers containing at least two terminal $CH_2<$ groups, including for example, butadiene, isoprene, divinyl benzene, divinyl naphthalene, allyl acrylates, and the like. These polymers are fully described in U.S. Pat. No. 2,798,053, to Brown, H. P., issued Jul. 2, 1957, this patent being incorporated herein by reference.

Examples of carboxylic acid copolymers useful in the present invention include Carbomer 934, Carbomer 941, Carbomer 950, Carbomer 951, Carbomer 954, Carbomer 980, Carbomer 981, Carbomer 1342, and Acrylates/$C_{10-30}$ Alkyl Acrylate Cross Polymers [available as Carbopol® 934, Carbopol® 941, Carbopol® 950, Carbopol® 951, Carbopol® 954, Carbopol® 980, Carbopol®981, Carbopol®1342, and the Pemulen Series (e.g. Pemulen TR1 and Pemulen TR2), respectively, from B. F. Goodrich].

Other carboxylic acid copolymers useful in the present invention include sodium salts of acrylic acid/acrylamide copolymers sold by the Hoechst Celanese Corporation under the trademark of Hostaceren PN73. Also included are the hydrogel polymers sold by Lipo Chemicals Inc. under the trademark of HYPAN hydrogels. These hydrogels consist of crystalline plicks of nitriles on a C-C backbone with various other pendant groups such as carboxyls, amides, and amidines. An example would include HYPAN SA100 H, a polymer powder available from Lipo Chemical.

The carboxylic acid copolymers can be used individually or as a mixture of two or more polymers and comprise from about 0.025% to about 2.00%, preferably from about 0.1% to about 1.50% and most preferably from about 0.40% to about 1.25% percent of the compositions of the present invention.

Paucilamellar Liposomal Vesicles

An essential component of the compositions of the instant invention is a paucilamellar lipid vesicle. Paucilamellar and other multilamellar lipid vesicles useful for incorporation into the emulsion compositions of the instant invention are known in the patent literature. These vesicles comprise several concentric lipid bilayers, encapsulating an internal aqueous phase. The vesicle bilayers can comprise a variety of lipid materials and surfactants. Typical vesicles useful in the present invention have approximately from two to eight lipid bilayers and range in diameter from about 100 nm to about 500. The following four patents, which are all incorporated herein by reference, describe these vesicles: U.S. Pat. No. 4,911,928 to Wallach, issued Mar. 27, 1990 discloses a method of making paucilamellar lipid vesicles; U.S. Pat. No. 4,855,090 to Wallach, issued Aug. 8, 1989 describes a method for preparing multilayered liposomes suitable for incorporating aqueous solutions of hydrophilic materials; U.S. Pat. No. 4,895,452 to Yiournas et al., issued Jan. 23, 1990 discloses an apparatus for the production of multilamellar and paucilamellar lipid vesicles; and WO 88/06883 to Wallach, published Sept. 22, 1988, discloses a method for producing paucilamellar lipid vesicles having an aqueous or organic liquid-filled cavity.

These vesicles are useful for incorporating the dihydroxyacetone used in the artificial tanning compositions of the instant invention. In a preferred method of making the tanning emulsions, the paucilamellar lipid vesicles, in the form of an aqueous dispersion, are added to and carefully mixed into a preformed oil-in-water emulsion containing the dihydroxyacetone. Without being limited by theory, it is believed that a portion of the dihydroxyacetone diffuses across the vesicle membranes to become encapsulated within the vesicles. The vesicle dispersion used in this method of preparation is obtained from Micro Vesicular Systems. Inc. (Nashua, N.H.) as their Novasome TM paucilamellar liposomal dispersion. The Examples given below illustrate this preparation method. Alternatively, vesicles already containing dihydroxyacetone can be first prepared and then subsequently incorporated into a preformed emulsion.

The paucilamellar lipid vesicles comprise from about 0.1% to about 20% on a dry weights basis of the emulsion compositions of the instant invention, more preferably from about 1% to about 10%, and most preferably from about 3% to about 45%. By the term "dry weights" basis is meant the weight percent of the vesicle components excluding the water phase and any water-phase components. The paucilamellar vesicles useful in the present invention comprise the following essential and optional components.

Polyoxyalkylene Alkyl Ether

A polyoxyalkylene alkyl ether is an essential component of the lipid vesicles employed in the instant invention. The polyoxyalkylene alkyl ether has the following structure

R—O—(CH$_2$—CH$_2$—O)$_n$—H where R is C$_{10}$-C$_{20}$ alkyl and n is an integer ranging from 1 to about 8. Preferred for use in the compositions of the instant invention are Ceteth-2, Ceteth-4, Ceteth 5, Ceteth-6, Laureth-1, Laureth-2, Laureth-3, Steareth-2, Steareth-4, Steareth-6, Ceteareth-2, Ceteareth-3, Ceteareth-4, Ceteareth-5, Ceteareth-6, and mixtures thereof. More preferred is Ceteth-2.

Sterol A sterol is an essential component of the lipid vesicles employed in the instant invention. Without being limited by theory, it is believed that the sterol provides better stability and buffers the thermotropic phase transition of the membrane layer. The sterol also provides optimum size control of the finished vesicle. Sterols are described in Hackh's Chemical Dictionary 4th ed., p. 638 (McGraw-Hill, New York; 1972), this reference being incorporated herein by reference. A preferred sterol for use in the vesicles of the instant invention is cholesterol.

Quaternary Ammonium Compound

Another essential component of the lipid vesicles employed in the instant invention is a quaternary ammonium compound. A cationic material such as a quaternary ammonium compound is incorporated in the lipid vesicle in order to yield a net positive charge. Without being limited by theory, it is believed that incorporation of such a charge-bearing material stabilizes the lipid structure and provides rapid dispersion. If such a charged material is not used, any vesicles formed may have a tendency to aggregate unless they are kept at very low concentrations. It is also believed, that incorporation of a charged material enhances the skin substantiveness of the liposomal vesicles, thereby aiding their distribution on the skin, and thus resulting in a more even tan delivery. The quaternary ammonium compound is selected from long chain amines and long chain pyridinium compounds. Examples of quaternary ammonium compounds useful in the instant invention include, but are not limited to, Quaternium-14, Quaternium-18, Quaternium-18 Methosulfate, cetyl trimethyl ammonium bromide, lapyrium chloride, steapyrium chloride, cetyl trimethyl ammonium chloride, cetyl trimethyl ammonium tosylate, lauryl pyridinium chloride, cetyl pyridinium chloride, dicetyldimonium chloride, distearyl dimethyl ammonium chloride, ditallow dimethyl ammonium chloride, and mixtures thereof. Preferred are the tetra alkyl ammonium compounds in which two of the alkyl substituents are methyl and the remaining two alkyl substituents are independently long chain alkyl moieties having from about 10 to about 22 carbon atoms. Examples of such preferred quaternary ammonium compounds include, but are not limited to, Quaternium-18, Quaternium-18 Methosulfate, dicetyldimonium chloride, distearyl dimethyl ammonium chloride, ditallow dimethyl ammonium chloride, and mixtures thereof. Most preferred is Quanternium-18.

Non-Surface Active Oil

An optional component of the lipid vesicles employed in the compositions of the instant invention is a non-surface active oil. By the term "non-surface" is meant that the oil does not possess surfactant or emulsification properties when incorporated into the liposomal vesicle and thus does not interefere with vesicle formation and stability. Examples of non-surface active oils useful for incorporation into the liposomal vesicles of the instant invention include, but are not limited to, mineral oil; silicone oils such as dimethicone, cyclomethicone, and the like; lipids; branched chain alcohols such as isostearyl alcohol and the like; branched chain hydrocarbons such as the Permethyl TM Series (available from The Permethyl Corporation, Frazer; Pa.); non-polar fatty acid and fatty alcohol esters and ethers; and mixtures thereof. See CTFA Cosmetic Ingredient Dictionary, Third Edition (1982), pp. 172–173; Hawley's Condensed Chemical Chemical Dictionary 11th ed., p. 704 (Van Nostrand Reinhold Co., New York; 1987); and U.S. Pat. No. 4,919,934, to Deckner et al., issued Apr. 24, 1990; these three references are incorporated herein by reference in their entirety.

A preferred non-surface active oil useful in the present invention is mineral oil, which is a liquid mixture of hydrocarbons derived from petroleum. Preferably the mineral oil comprises from about 10% to about 50% of the lipid vesicles. More preferably the mineral oil comprises about 50% of the lipid vesicles.

Preferred Paucilamellar Lipid Vesicles

A preferred paucilamellar lipid vesicle useful in the emulsions of the instant invention is a liposomal dispersion in water of cholesterol, Quaternium-18, Ceteth-2, and optionally, mineral oil [obtained from Micro Vesicular Systems (Nashua, H.H.) as their Novasome ™ liposomal dispersion]. This preferred lipid vesicle comprises from about 2 to about 8 lipid bilayers with a diameter ranging from about 100 nm to about 500 nm, and comprises from about 0.1% to about 20% on a dry weights basis of the emulsion compositions of the instant invention. Preferably the lipid vesicles comprise from about 1% to about 10% of the emulsion compositions. Most preferably the lipid vesicles comprise from about 3% to about 4% of the emulsion compositions.

Optional Components

Each of the water and oil phases of the oil-in-water emulsions can comprise a wide variety of optional components. Typical of such optional components are:

Sunscreens

A wide variety of one or more conventional sunscreening agents are suitable for use in the present invention. Segarin, et al., at Chapter VIII, pages 189 et seq., of *Cosmetics Science and Technology*, disclose numerous suitable agents. Specific suitable sunscreening agents include, but are not limited to, for example: Ethylhexyl-p-methoxycinnamate (available as Parsol MCX from Givaudan Corporation), p-Aminobenzoic acid, its salt and its derivatives (ethyl, isobutyl, glyceryl esters; p-dimethylaminobenzoic acid; 2-ethylhexyl N,N-dimethylaminobenzoate); p-Methoxycinnamic Acid Diethanolamine Salt (available as Bernel Hydro from Bernel Chemical Co.); Anthranilates (i.e., o-aminobenzoates; methyl, octyl, amyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, -phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); dibenzalacetone and benzalacetophenone; 2-Phenyl-benzimidazole-5-sulfonic acid and its salts;

Naphtholsulfonates (sodium salts of 2-naphthol 3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl napthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2′,4,4′-Tetrahydroxybenzophenone, 2,2′-Dihydroxy-4,4′-dimethoxybenzophenone, Octabenzone; 4-Isopropyldibenzoylmethane; Butylmethoxydibenzoylmethane; Octocrylene; 4-isopropyldi-benzoylmethane; and camphor derivatives such as methyl benzylidene or benzylidene camphor; and mixtures thereof. Other sunscreens include the solid physical sunblocks such as titanium dioxide (micronized titanium dioxide, 0.03 microns, 0.035 microns, 0.050 microns, and other suitable sizes), zinc oxide, silica, iron oxide and the like. Without being limited by theory, it is believed that the inorganic materials provide a sunscreening benefit through reflecting, scattering, and absorbing harmful UV, visible, and infrared radiation.

Typically, a safe and photoprotectively effective amount of sunscreen(s) can be used in the artificial tanning emulsions of the present invention. By "safe and photoprotectively" is meant an amount sufficient to provide photoprotection when the composition is applied, but no so much as to cause any side effects or skin reactions. Generally, the sunscreen(s) can comprise from about 0.5% to about 20% of the composition. Exact amounts will vary depending upon the sunscreen chosen and the desired Sun Protection Factor (SPF). SPF is a commonly used measure of photoprotection of a sunscreen against erythema. See Federal Register, Vol. 43, No. 166, pp. 38206–38269, Aug. 25, 1978.

Other useful sunscreens are those disclosed in U.S. Pat. No. 4,937,370, to Sabatelli, issued Jun. 26, 1990; and U.S. Pat. No. 4,999,186 to Sabatelli et al., issued Mar. 12, 1991; these two references being incorporated by reference herein. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

These sunscreening agents provide higher efficacy, broader UV absorption, lower skin penetration and longer lasting efficacy relative to conventional sunscreens.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl) methylaminobenzoic acid ester of 4-(2-hydroxyethoxy)dibenzoylmethane; N-N-di-(2-ethylhexyl)-4-aminobenzoic acid ester of 2-hydroxy-4-(2-hydroxyethoxy)benzophenone; and N,N-di-(2-ethylhexyl)4-aminobenzoic acid ester of 4-(2-hydroxyethoxy)dibenzoylmethane; and mixtures thereof.

Humectants/Moisturizers

The artificial tanning compositions of the instant invention can also contain one or more humectants/moisturizers. A variety of humectants/moisturizers can be employed and can be present at a level of from about 1% to about 30%, more preferably from about 2% to about 8% and most preferably from about 3% to about 5%. These materials include, but are not limited to, urea; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerin, hexanetriol, propylene glycol, hexylene glycol and the like; polyethylene glycol; sugars and starches; sugar and starch derivatives (e.g. alkoxylated gluclose); panthenol (including D-, L-, and the D,L-forms); pyrrolidone carboxylic acid; hyaluronic acid;

lactamide monoethanolamine; acetamide monoethanolamine; and mixtures thereof.

Preferred humectants/moisturizers for use in the compositions of the present invention are the $C_3$–$C_6$ diols and triols. Especially preferred is the triol, glycerin.

Emollients

The compositions of the present invention can also optionally comprise at least one emollient. Examples of suitable emollients include, but are not limited to, volatile and non-volatile silicone oils, highly branched hydrocarbons, and non-polar fatty acid and fatty alcohol esters, and mixtures thereof. Emollients useful in the instant invention are further described in U.S. Pat. No. 4,919,934, to Deckner et al., issued Apr. 24, 1990, which is incorporated herein by reference in its entirety.

The emollients can typically comprise in total from about 1% to about 50%, preferably from about 1% to about 25%, and more preferably from about 1% to about 10% by weight of the compositions of the present invention.

Vitamins

Various vitamins can also be included in the compositions of the present invention. Non-limiting examples include Vitamin A, and derivatives thereof, ascorbic acid, Vitamin B complexes and derivatives thereof such as panthothenic acid, biotin, Vitamin D, Vitamin E and derivatives thereof such as tocopheryl acetate, and mixtures thereof can also be used.

Other Optional Components

A variety of additional ingredients can be incorporated into the emulsion compositions of the present invention. Non-limiting examples of these additional ingredients include various polymers for aiding the film-forming properties and substantivity of the formulations; resins; preservatives for maintaining the antimicrobial integrity of the compositions; antioxidants; skin soothing and healing agents such as aloe vera extract, allantoin and the like; chelators and sequestrants; agents suitable for aesthetic purposes such as fragrances, pigments, and colorings; and other cosmetic ingredients such as eucalyptus, chamomile extract, guava extract, lanolin, cocoa butter, and palm oil.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLE I

Artificial Tanning Cream

An oil-in-water emulsion is prepared by combining the following components utilizing conventional mixing techniques.

| Ingredients | % Weight |
| --- | --- |
| Phase A | |
| Water | qs 100 |
| Magnesium Aluminum Silicate | 0.50 |
| Xanthan Gum | 0.30 |
| Disodium EDTA | 0.10 |
| Allantoin | 0.20 |
| Glycerin | 2.50 |
| Sodium Metabisulfite | 0.005 |
| Phase B | |
| Cetyl Alcohol | 2.00 |
| Stearyl Alcohol | 2.00 |
| $C_{12-15}$ Alcohols Benzoate | 3.00 |
| Octyl Palmitate | 3.00 |
| Dimethicone | 1.00 |
| Polysorbate 60 | 1.00 |
| Steareth-20 | 1.00 |
| Glyceryl Stearate (and) PEG-100 Stearate | 0.25 |
| PPG-20 Methyl Glucose Ether Distearate | 2.00 |
| Actiplex 335[1] | 0.10 |
| Phase C | |
| Butylene Glycol | 2.50 |
| DMDM Hydantoin (and) Iodopropynyl Butylcarbamate | 0.25 |
| Phase D | |
| Fragrance | 0.15 |
| Phase E | |
| Dihydroxyacetone | 3.00 |
| Phase F | |
| Paucilamellar Vesicle Dispersion[2] | 15.00 |

[1]Contains a mixture of aloe vera extract, eucalyptus, chamomile extract, guava extract, lanolin, cocoa butter, and palm oil dissolved in mineral oil. Obtained from Active Organics, Inc. (Van Nuys, CA).
[2]Contains a liposomal dispersion in water of cholesterol, Quaternium-18, Ceteth-2, and mineral oil. Obtained from Micro Vesicular Systems (Nashua, NH) as Novasome ™ liposomal dispersion.

In a suitable vessel the Phase A ingredients are dispersed in the water and heated to 75°–85° C. In a separate vessel the Phase B ingredients are combined and heated to 85°–90° C. until melted. This mixture is then added to Phase A to form the emulsion. The emulsion is cooled to 40°–45° C. with continued mixing. Next, in a separate vessel, the Phase C ingredients are heated with mixing to 40°–45° C. until a clear solution is formed and this solution is then added to the emulsion. The fragrance, Phase D, is then added to the emulsion with mixing. Next, in a separate vessel, the dihydroxyacetone is dissolved in water, Phase E, and the resulting solution is mixed into the emulsion. Finally, the paucilamellar vesicle dispersion, Phase F, is carefully mixed into the emulsion, which is then cooled to 30°–35° C., and then to room temperature.

This emulsion is useful for topical application to the skin to provide an artificial tan.

EXAMPLE II

Artificial Tanning Cream

An oil-in-water emulsion is prepared by combining the following components utilizing conventional mixing techniques.

| Ingredients | % Weight |
| --- | --- |
| Water | qs 100 |
| Magnesium Aluminum Silicate | 0.50 |
| Xanthan Gum | 0.30 |
| Disodium EDTA | 0.10 |
| Allantoin | 0.20 |
| Glycerin | 2.50 |
| Sodium Metabisulfite | 0.005 |
| Phase B | |
| Cetyl Alcohol | 2.00 |
| Stearyl Alcohol | 2.00 |
| $C_{12-15}$ Alcohols Benzoate | 3.00 |
| Octyl Palmitate | 3.00 |
| Dimethicone | 1.00 |
| Polysorbate 60 | 1.00 |

| Ingredients | % Weight |
|---|---|
| Steareth-20 | 1.00 |
| Glyceryl Stearate (and) PEG-100 Stearate | 0.25 |
| PPG-20 Methyl Glucose Ether Distearate | 2.00 |
| Actiplex 335 | 0.10 |
| Phase C | |
| Butylene Glycol | 2.50 |
| DMDM Hydantoin (and) Iodopropynyl Butylcarbamate | 0.25 |
| Phase D | |
| Fragrance | 0.15 |
| Phase E | |
| Dihydroxyacetone | 4.00 |
| Phase F | |
| Paucilamellar Vesicle Dispersion | 20.00 |

An emulsion is prepared from the above ingredients employing the method described in Example I.

This emulsion is useful for topical application to the skin to provide an artificial tan.

EXAMPLE III

Artificial Tanning Cream

An oil-in-water emulsion is prepared by combining the following components utilizing conventional mixing techniques.

| Ingredients | % Weight |
|---|---|
| Phase A | |
| Water | qs 100 |
| Magnesium Aluminum Silicate | 0.50 |
| Xanthan Gum | 0.30 |
| Disodium EDTA | 0.10 |
| Allantoin | 0.20 |
| Glycerin | 2.50 |
| Carbomer 934[1] | 0.30 |
| Carbomer 1342[2] | 0.30 |
| Sodium Metabisulfite | 0.005 |
| Phase B | |
| Cetyl Alcohol | 2.00 |
| Stearyl Alcohol | 2.00 |
| $C_{12-15}$ Alcohols Benzoate | 3.00 |
| Octyl Palmitate | 3.00 |
| Dimethicone | 1.00 |
| Polysorbate 60 | 1.00 |
| Steareth-20 | 1.00 |
| Glyceryl Stearate (and) PEG-100 Stearate | 0.25 |
| Actiplex 335 | 0.10 |
| PPG-20 Methyl Glucose Ether Distearate | 2.00 |
| DEA-Cetyl Phosphate | 0.50 |
| Phase C | |
| Butylene Glycol | 2.50 |
| DMDM Hydantoin (and) Iodopropynyl Butylcarbamate | 0.25 |
| Phase D | |
| Fragrance | 0.15 |
| Phase E | |
| Dihydroxyacetone | 3.00 |
| Phase F | |
| Paucilamellar Vesicle Dispersion | 15.00 |

[1]Available as Carbopol ® 934 from B. F. Goodrich.
[2]Available as Carbopol ® 1342 from B. F. Goodrich.

An emulsion is prepared from the above ingredients employing the method described in Example I.

This emulsion is useful for topical application to the skin to provide an artificial tan.

EXAMPLE IV

Artificial Tanning Cream

An oil-in-water emulsion is prepared by combining the following components utilizing conventional mixing techniques.

| Ingredients | % Weight |
|---|---|
| Phase A | |
| Water | qs 100 |
| Magnesium Aluminum Silicate | 0.50 |
| Xanthan Gum | 0.30 |
| Disodium EDTA | 0.10 |
| Allantoin | 0.20 |
| Glycerin | 2.50 |
| Sodium Metabisulfite | 0.005 |
| Phase B | |
| Cetyl Alcohol | 2.00 |
| Stearyl Alcohol | 2.00 |
| $C_{12-15}$ Alcohols Benzoate | 3.00 |
| Octyl Palmitate | 3.00 |
| Dimethicone | 1.00 |
| Actiplex 335 | 0.10 |
| PPG-20 Methyl Glucose Ether Distearate | 2.00 |
| DEA-Cetyl Phosphate | 1.00 |
| Phase C | |
| Butylene Glycol | 2.50 |
| DMDM Hydantoin (and) Iodopropynyl Butylcarbamate | 0.25 |
| Phase D | |
| Fragrance | 0.15 |
| Phase E | |
| Dihydroxyacetone | 3.00 |
| Phase F | |
| Paucilamellar Vesicle Dispersion | 15.00 |

An emulsion is prepared from the above ingredients employing the method described in Example I.

This emulsion is useful for topical application to the skin to provide an artificial tan.

EXAMPLE V

Artificial Tanning Cream

An oil-in-water emulsion is prepared by combining the following components utilizing conventional mixing techniques.

| Ingredients | % Weight |
|---|---|
| Phase A | |
| Water | qs 100 |
| Disodium EDTA | 0.10 |
| Allantoin | 0.20 |
| Glycerin | 2.50 |
| Sodium Metabisulfite | 0.005 |
| Phase B | |
| Cetyl Alcohol | 2.00 |
| Stearyl Alcohol | 2.00 |
| Dimethicone | 1.00 |
| Distearyl Dimethyl Ammonium Chloride | 2.00 |
| Actiplex 335 | 0.10 |
| PPG-20 Methyl Glucose Ether Distearate | 2.00 |
| Phase C | |
| Butylene Glycol | 2.50 |
| DMDM Hydantoin (and) Iodopropynyl Butylcarbamate | 0.25 |
| Phase D | |
| Fragrance | 0.15 |
| Phase E | |
| Dihydroxyacetone | 3.00 |
| Phase F | |
| Paucilamellar Vesicle Dispersion | 15.00 |

This emulsion is useful for topical application to the skin to provide an artificial tan.

EXAMPLE VI

Artificial Tanning Cream

An oil-in-water emulsion is prepared by combining the following components utilizing conventional mixing techniques.

| Ingredients | % Weight |
|---|---|
| Phase A | |
| Water | qs 100 |
| Magnesium Aluminum Silicate | 0.50 |
| Xanthan Gum | 0.30 |
| Disodium EDTA | 0.10 |
| Allantoin | 0.20 |
| Glycerin | 2.50 |
| Carbomer 980[1] | 0.30 |
| Acrylates/C$_{10-30}$ Alkyl Acrylate Crosspolymer[2] | 0.30 |
| Sodium Metabisulfite | 0.005 |
| Phase B | |
| Cetyl Alcohol | 2.00 |
| Stearyl Alcohol | 2.00 |
| C$_{12-15}$ Alcohols Benzoate | 3.00 |
| Octyl Palmitate | 3.00 |
| Dimethicone | 1.00 |
| Polysorbate 60 | 1.00 |
| Steareth-20 | 1.00 |
| Glyceryl Stearate (and) PEG-100 Stearate | 0.25 |
| Actiplex 335 | 0.10 |
| PPG-20 Methyl Glucose Ether Distearate | 2.00 |
| DEA-Cetyl Phosphate | 0.50 |
| Phase C | |
| Butylene Glycol | 2.50 |
| DMDM Hydantoin (and) Iodopropynyl Butylcarbamate | 0.25 |
| Phase D | |
| Fragrance | 0.15 |
| Phase E | |
| Dihydroxyacetone | 3.00 |
| Phase F | |
| Paucilamellar Vesicle Dispersion | 15.00 |

[1] Available as Carbopol ® 980 from B. F. Goodrich.
[2] Available as Pemulen TR1 from B. F. Goodrich.

An emulsion is prepared from the above ingredients employing the method described in Example I.

This emulsion is useful for topical application to the skin to provide an artificial tan.

EXAMPLE VII

High SPF Artificial Tanning Cream

An oil-in-water emulsion is prepared by combining the following components utilizing conventional mixing techniques.

| Ingredients | % Weight |
|---|---|
| Phase A | |
| Water | qs 100 |
| Magnesium Aluminum Silicate | 0.50 |
| Xanthan Gum | 0.30 |
| Disodium EDTA | 0.10 |
| Allantoin | 0.20 |
| Glycerin | 2.50 |
| Sodium Metabisulfite | 0.005 |
| Phase B | |
| Octyl Methoxycinnamate | 7.50 |
| Octocrylene | 4.00 |
| Cetyl Alcohol | 2.00 |
| Stearyl Alcohol | 2.00 |
| C$_{12-15}$ Alcohols Benzoate | 3.00 |
| Octyl Palmitate | 3.00 |
| Dimethicone | 1.00 |
| Polysorbate 60 | 1.00 |
| Steareth-20 | 1.00 |
| Glyceryl Stearate (and) PEG-100 Stearate | 0.25 |
| Actiplex 335 | 0.10 |
| PPG-20 Methyl Glucose Ether Distearate | 2.00 |
| Phase C | |
| Butylene Glycol | 2.50 |
| DMDM Hydantoin (and) Iodopropynyl Butylcarbamate | 0.25 |
| Phase D | |
| Fragrance | 0.15 |
| Phase E | |
| Dihydroxyacetone | 3.00 |
| Phase F | |
| Paucilamellar Vesicle Dispersion | 15.00 |

An emulsion is prepared from the above ingredients employing the method described in Example I.

This emulsion is useful for topical application to the skin to provide an artificial tan and to provide protection to the skin from the harmful effects of ultraviolet radiation.

What is claimed is:

1. An artificial tanning oil-in-water emulsion composition having a pH from about 2.5 to about 7, comprising:
   (a) from about 1% to about 50% of an oil phase;
   (b) from about 0.1% to about 10% of at least one emulsifier;
   (c) from about 0.1% to about 5% of at least one thickener;
   (d) from about 10% to about 95% of an aqueous phase;
   (e) from about 0.1% to about 20% of dihydroxyacetone; and
   (f) from about 0.1% to about 20% on a dry weights basis of paucilamellar liposomal vesicles having a diameter of from about 100 nm to about 500 nm, said vesicles being dispersed in the aqueous phase (d) and wherein said vesicles comprise a polyoxyalkylene alkyl ether, a sterol, and a quaternary ammonium compound and further wherein said vesicles encapsulate an internal aqueous phase.

2. The emulsion composition according to claim 1 wherein said paucilamellar liposomal vesicles comprise on a dry weights basis from about 1% to about 10% of the emulsion composition.

3. The emulsion composition according to claim 2 wherein said paucilamellar liposomal vesicles comprise on a dry weights basis from about 3% to about 4% of the emulsion composition.

4. The emulsion composition according to claim 3 wherein said polyoxyalkylene alkyl ether has the structure $$R-O-(CH_2-CH_2-O)_n-H$$

where R is C$_{10}$-C$_{20}$ alkyl and n is an integer ranging from 1 to about 8.

5. The emulsion composition according to claim 4 wherein said polyoxyalkylene alkyl ether is selected from the group consisting of Ceteth-2, Ceteth-4, Ceteth-5, Ceteth-6, Laureth-1, Laureth-2, Laureth-3, Steareth-2, Steareth-4, Steareth-6, Ceteareth-2, Ceteareth-3, Ceteareth-4, Ceteareth-5, Ceteareth-6, and mixtures thereof.

6. The emulsion composition according to claim 5 wherein said polyoxyalkylene alkyl ether is Ceteth-2.

7. The emulsion composition according to claim 6 wherein said sterol is cholesterol.

8. The emulsion composition according to claim 7 wherein said quaternary ammonium compound is selected from the group consisting of Quaternium-14, Quaternium-18, Quaternium-18 Methosulfate, cetyl trimethyl ammonium bromide, cetyl trimethyl ammonium chloride, cetyl trimethyl ammonium tosylate, lauryl pyridinium chloride, cetyl pyridinium chloride, and mixtures thereof.

9. The emulsion composition according to claim 8 wherein said quaternary ammonium compound is selected from the group consisting of Quaternium-18, Quaternium-18 Methosulfate, dicetyldimonium chloride, distearyl dimethyl ammonium chloride, ditallow dimethyl ammonium chloride, and mixtures thereof.

10. The emulsion composition according to claim 9 wherein said quaternary ammonium compound is Quaternium-18.

11. The emulsion composition according to claim 10 wherein said emulsifier is selected from the group consisting of esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

12. The emulsion composition according to claim 11 wherein said emulsifier is selected from the group consisting of polyethylene glycol 20 sorbitan monolaurate (Polysorbate 20), polyethylene glycol 5 soya sterol, Steareth-20, Ceteareth-20, Ceteth-10, Polysorbate 80, cetyl phosphate, potassium cetyl phosphate, diethanolamine cetyl phosphate, Polysorbate 60, glyceral stearate, PEG-100 Stearate, PPG-20 methyl glucose ether distearate, Carbomer 954, Carbomer 980, Carbomer 1342, Acrylates/$C_{10-30}$ Alkyl Acrylate Crosspolymer (Pemulen TR1), Acrylates/$C_{10-30}$ Alkyl Acrylate Crosspolymer (Pemulen TR2), and mixtures thereof.

13. The emulsion according to claim 12 wherein said thickener is selected from the group consisting of xanthan gum, magnesium aluminum silicate, guar gum, kelp, algin and alginate salts, hydroxypropylcellulose, hydroxyethylcellulose, carboxymethylcellulose, methylcellulose, ethylcellulose, and mixtures thereof.

14. The emulsion composition according to claim 13 wherein said dihydroxyacetone comprises from about 2% to about 7% of the emulsion composition.

15. The emulsion composition according to claim 14 wherein said dihydroxyacetone comprises from about 3% to about 5% of the emulsion composition.

16. The emulsion composition according to claim 15 wherein said composition has a pH from about 3 to about 6.

17. The emulsion composition according to claim 16 wherein said composition has a pH from about 3 to about 4.5.

18. The emulsion composition according to claim 17 wherein said composition further comprises from about 0.5% to about 20% of at least one sunscreen agent selected from the group consisting of ethylhexyl-p-methoxycinnamate, octyl salicylate, octocrylene, 2-ethylhexyl N,N-dimethylaminobenzoate, 2-phenyl-benzimidazole-5-sulfonic acid, 4-N,N-(2-ethylhexyl)methylaminobenzoic acid ester of 2,4-dihydroxybenzophenone, N,N-di-(2-ethylhexyl)-4-aminobenzoic acid ester with 4-hydroxydibenzoylmethane, 4-N,N(2-ethylhexyl) methylaminobenzoic acid ester with 4-hydroxydibenzoylmethane, 4N,N-(2-ethylhexyl)methylaminobenzoic acid ester of 2-hydroxy-4-(2-hydroxyethoxy)benzophenone, 4-N,N-(2-ethylhexyl) methylaminobenzoic acid ester of 4-(2-hydroxyethoxy)dibenzoylmethane, N-N-di-(2-ethylhexyl)-4-aminobenzoic acid ester of 2-hydroxy-4-(2-hydroxyethoxy)benzophenone, N,N-di-(2-ethylhexyl)4-aminobenzoic acid ester of 4-(2-hydroxyethoxy)dibenzoylmethane, titanium dioxide, zinc oxide, and mixtures thereof.

19. The emulsion composition according to claim 18 wherein said sunscreen agent is selected from the group consisting of ethylhexyl-p-methoxycinnamate, octocrylene, octyl salicylate, 2-phenyl-benzimidazole-5-sulfonic acid, titanium dioxide, and mixtures thereof.

20. The emulsion composition according to claim 1 wherein said liposomal vesicles further comprise from about 10% to about 50% of a non-surface active oil.

21. The emulsion composition according to claim 20 wherein said liposomal vesicles comprise about 50% of a non-surface active oil.

22. The emulsion composition according to claim 21 wherein said non-surface active oil is mineral oil.

23. The emulsion composition according to claim 22 wherein said composition further comprises from about 0.5% to about 20% of at least one sunscreen agent selected from the group consisting of ethylhexyl-p-methoxycinnamate, octyl salicylate, octocrylene, 2-ethylhexyl N,N-dimethylaminobenzoate, 2-phenyl-benzimidazole-5-sulfonic acid, 4-N,N-(2-ethylhexyl)methylaminobenzoic acid ester of 2,4-dihydroxybenzophenone, N,N-di-(2-ethylhexyl)-4-aminobenzoic acid ester with 4-hydroxydibenzoylmethane, 4-N,N(2-ethylhexyl) methylaminobenzoic acid ester with 4-hydroxydibenzoylmethane, 4-N,N-(2-ethylhexyl)methylaminobenzoic acid ester of 2-hydroxy-4-(2-hydroxyethoxy)benzophenone, 4-N,N-(2-ethylhexyl) methylaminobenzoic acid ester of 4-(2-hydroxyethoxy)dibenzoylmethane, N-N-di-(2-ethylhexyl)-4-aminobenzoic acid ester of 2-hydroxy-4-(2-hydroxyethoxy)benzophenone, N,N-di-(2-ethylhexyl)4-aminobenzoic acid ester of 4-(2hydroxyethoxy)dibenzoylmethane, titanium dioxide, zinc oxide, and mixtures thereof.

24. The emulsion composition according to claim 23 wherein said sunscreen agent is selected from the group consisting of ethylhexyl-p-methoxycinnamate, octocrylene, octyl salicylate, 2-phenyl-benzimidazole-5-sulfonic acid, titanium, dioxide, and mixtures thereof.

25. A method for providing an artificial tan to human skin, said method comprising topically applying to the skin of the human an effective amount of an emulsion composition according to claim 1.

26. A method for providing both an artificial tan to human skin and protecting human skin from the effects of ultraviolet radiation, said method comprising topically applying to the skin of the human an effective amount of an emulsion composition according to claim 19.

27. A method for providing an artificial tan to human skin, said method comprising topically applying to the skin of the human an effective amount of an emulsion composition according to claim 22.

28. A method for providing both an artificial tan to human skin and protecting human skin from the effects of ultraviolet radiation, said method comprising topically applying to the skin of the human an effective amount of an emulsion composition according to claim 24.

* * * * *